US010813569B2

(12) United States Patent
Forman et al.

(10) Patent No.: US 10,813,569 B2
(45) Date of Patent: Oct. 27, 2020

(54) MOTION CORRECTION IN MAGNETIC RESONANCE IMAGING

(71) Applicant: Siemens Healthcare GmbH, Erlangen (DE)

(72) Inventors: Christoph Forman, Erlangen (DE); Peter Speier, Erlangen (DE); Marcel Dominik Nickel, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 94 days.

(21) Appl. No.: 15/978,326

(22) Filed: May 14, 2018

(65) Prior Publication Data
US 2018/0333067 A1 Nov. 22, 2018

(30) Foreign Application Priority Data

May 17, 2017 (EP) ..................................... 17171531

(51) Int. Cl.
A61B 5/055 (2006.01)
A61B 5/05 (2006.01)
G01R 33/563 (2006.01)
G01R 33/565 (2006.01)
(Continued)

(52) U.S. Cl.
CPC ............ A61B 5/055 (2013.01); A61B 5/0515 (2013.01); G01R 33/5611 (2013.01); G01R 33/56308 (2013.01); G01R 33/56509 (2013.01); G01R 33/5676 (2013.01)

(58) Field of Classification Search
CPC ... A61B 5/0515; A61B 5/055; G01R 33/5611; G01R 33/56308; G01R 33/56509; G01R 33/5676
See application file for complete search history.

(56) References Cited

U.S. PATENT DOCUMENTS

| 8,195,275 B2 | 6/2012 | Zwick et al. |
| 2011/0031971 A1 | 2/2011 | Deimling et al. |
| 2013/0197347 A1 | 8/2013 | Moghari et al. |

(Continued)

FOREIGN PATENT DOCUMENTS

DE 102009036237 A1 9/2011

OTHER PUBLICATIONS

European Search Report for related European Application No. EP 17171531, dated Dec. 8, 2017.
(Continued)

Primary Examiner — Rishi R Patel
(74) Attorney, Agent, or Firm — Lempia Summerfield Katz LLC

(57) ABSTRACT

A method for reconstructing dynamic image data is described. In the method, raw data is acquired in a time-dependent manner from an examination region, wherein at least some of the raw data is assigned various values of movement parameters. First time-dependent image data based on acquired raw data is reconstructed. Furthermore, deformation fields based on the first image data are determined as a function of at least two time-dependent movement parameters. Based on the deformation fields, the raw data and the first image data, corrected image data is then generated. Furthermore, a reconstruction apparatus is described. Moreover, a magnetic resonance imaging system is described.

15 Claims, 4 Drawing Sheets

(51) Int. Cl.
*G01R 33/561* (2006.01)
*G01R 33/567* (2006.01)

(56) References Cited

U.S. PATENT DOCUMENTS

2014/0301622 A1* 10/2014 Forman ................. G06T 11/005
382/131
2015/0015691 A1 1/2015 Forman et al.

OTHER PUBLICATIONS

M. Salman Asif et al: "Motion-adaptive spatio-temporal regularization for accelerated dynamic MRI", Magnetic Resonance in Medicine, Bd. 70, Nr. 3, pp. 800-812, (2012).

* cited by examiner

MOTION CORRECTION IN MAGNETIC RESONANCE IMAGING

The application claims the benefit of European Patent Application No. EP 17171531.1, filed May 17, 2017, which is hereby incorporated by reference in its entirety.

TECHNICAL FIELD

The disclosure relates to a method for reconstructing dynamic image data. Moreover, the disclosure also relates to an image reconstruction apparatus. Furthermore, the disclosure relates to a magnetic resonance system.

BACKGROUND

With the aid of modern imaging methods, two or three-dimensional image data or time series of image data are frequently generated, which may be used for visualizing an imaged examination object. Imaging systems based on a method of magnetic resonance measurement, (particularly of nuclear spin, so-called magnetic resonance tomographs), have successfully established themselves and proven their worth through a wide range of applications. With this kind of image acquisition, a static basic magnetic field $B_0$, which is used for the initial alignment and homogenization of magnetic dipoles for examination, may be superimposed with a fast-switched magnetic field, the so-called gradient field for local resolution of the imaging signal. To determine the material properties of an examination object for imaging, the dephasing and/or relaxation time after a deflection of the magnetization from the initial alignment is determined such that various relaxation mechanisms and/or relaxation times of materials may be identified.

Deflection may take place by a number of RF pulses, and local resolution is based on a timed manipulation of the deflected magnetization with the aid of the gradient field in a so-called measurement sequence and/or control sequence which establishes a precise chronological sequence of RF pulses, the change in the gradient field (by emitting a switching sequence of gradient pulses) and the recording of measured values. Besides relaxation, there are also a series of further mechanisms for contrast formation such as, for example, flow measurement and diffusion imaging.

An assignment may take place between measured magnetization, from which the aforementioned material properties may be derived, and a location coordinate of the measured magnetization in the local area in which the examination object is arranged, with the aid of an intermediate stage. In this intermediate stage, recorded magnetic resonance raw data is arranged at readout points in the so-called "k-space", wherein the coordinates of the k-space are encoded as a function of the gradient field. The amount of magnetization (in particular, of transverse magnetization, determined in a plane transverse to the basic magnetic field described above) at a particular location of the examination object may be determined from the k-space data with the aid of a Fourier transformation. In other words, the k-space data (e.g., Magnitude and Phase) is required to calculate a signal strength of the signal and if applicable, its phase in the local area.

Magnetic resonance imaging is also used for the image recording of moved examination regions. Examples of this are MR angiography and dynamic contrast-enhanced magnetic resonance imaging (DCE-MRI), which are described by way of example in DE Patent Publication No. 102009036237 A1 or U.S. Pat. No. 8,195,275 B2. When acquiring raw data, at certain times only sub-sampled raw data is recorded such that to reconstruct image data at a certain time, data from other times is also included which, however, is recorded in another movement state of the examination region. To nevertheless provide the joint use of items of raw data acquired at different times, it is assumed that changes in the area for imaging between the individual times have only an insignificant effect on imaging. In the case of greater dynamics in the image area, however, this assumption is no longer justified so that movement artifacts appear in the reconstructed images.

In the literature, approaches taking into account movement in image reconstruction are described. For example, a higher consistency in the raw data acquired at various times and the image data reconstructed from it may be achieved by applying deformation fields. Some approaches take into account the movement in an iterative reconstruction of image data. However, only one dimension, (e.g., either only the time or only the different movement states), is taken into account. For example, in time-resolved imaging the fields of movement are calculated in a first reconstruction of image data and taken into account in a subsequent second reconstruction.

SUMMARY AND DESCRIPTION

The scope of the present disclosure is defined solely by the appended claims and is not affected to any degree by the statements within this summary. The present embodiments may obviate one or more of the drawbacks or limitations in the related art.

It is an object of the present disclosure to develop a method for reconstructing dynamic MR image data which enables an improved correction of movement artifacts.

This object is achieved by a method for reconstructing dynamic image data, an image reconstruction apparatus, and by a magnetic resonance imaging system.

In the method for reconstructing dynamic image data, time-dependent raw data is acquired from an examination region, wherein at least some of the raw data is associated with different values of movement parameters. In this context, dynamic image data should be understood as image data from a moved object which is recorded over a predetermined period. The term "movement parameters" should be understood in this context to refer to variables which have an influence on a movement state. Examples of this are, for example, the time, the respiratory condition, or the heart movement condition. "Time-dependent acquisition" should be understood to mean that different times are assigned to individual k-space points of the raw data and a set of successively measured k-space points is combined to form the calculated times.

To obtain information about an assignment of raw data to individual movement states, in addition, for example, navigator raw data may be acquired and reconstructed to form navigator image data. The navigator image data characterizes movement states of the examination region for imaging. Based on the movement states now known and the acquired raw data, raw data may then be assigned to individual movement states, (e.g., raw data $RD_1$ assigned according to the movement state is therefore generated).

Based on the acquired raw data, first, time-dependent image data is reconstructed. For example, image data for a plurality of different points in time is reconstructed. Based on the first image data, deformation fields are then determined as a function of at least two time-dependent movement parameters. Deformation fields provide information about a shift of a point of an examination region as a function of the aforementioned movement parameters, for example, the time and the respiratory condition or the heart movement condition. Finally, corrected image data is determined on the basis of the deformation fields of the raw data and the first image data.

With the aid of the deformation fields, parts of the first image data assigned to different movement parameter values are registered on top of each other to obtain more image information for each parameter value. Based on the more precise image information, improved deformation fields may then be generated, for example, within the framework of an iteration, (e.g., an iterative image reconstruction), with the help of which more precise image data, (e.g., "corrected" image data may be reconstructed in turn). Therefore, even with strong sub-sampling, which may occur with magnetic resonance-image recordings of moved objects, image data may be generated with improved accuracy and/or with reduced artifacts.

The image reconstruction apparatus includes an input interface for receiving raw data acquired in a time-dependent manner from an examination region, wherein at least some of the raw data is assigned to different values of movement parameters. Part of the image reconstruction apparatus is also a reconstruction unit for reconstructing first time-dependent image data based on acquired raw data. The image reconstruction apparatus also includes a deformation field determination unit for determining deformation fields based on first image data as a function of at least two time-dependent movement parameters and a correction unit for generating corrected image data based on deformation fields, the raw data, and the first image data.

The magnetic resonance imaging system includes a control device configured to control the magnetic resonance imaging system using the method. The magnetic resonance imaging system may include the image reconstruction apparatus disclosed herein for this purpose.

The components of the image reconstruction apparatus may be predominantly configured in the form of software components. In particular, this concerns the reconstruction unit, the deformation field determination unit, and the correction unit. In principle, however, these components may also be partly realized, in particular, where particularly fast calculations are involved, in the form of software-supported hardware, (e.g., field programmable gate arrays (FPGAs) or the like). Likewise, the required interfaces, for example, where only a transfer of data from other software components is involved, may be designed as software interfaces. However, they may also be designed as hardware-based interfaces which are controlled by suitable software.

In particular, the image reconstruction apparatus may be part of a user terminal and/or a control device of a magnetic resonance imaging system.

A largely software-based implementation has the advantage that even image reconstruction apparatuses and/or control devices used hitherto may be simply upgraded by a software update to work in the manner according to the embodiments disclosed herein. In this respect, the object is also achieved by a corresponding computer program product with a computer program that may be loaded directly into a storage device of a control device of a magnetic resonance imaging system, with program sections to perform the acts of the method when the program is executed in the control device. In addition to the computer program, such a computer program product may include additional components such as documentation and/or additional components as well as hardware components such as hardware keys (e.g., dongles, etc.) to use the software.

For transport to the control device and/or for storage on or in the control device, a computer-readable medium, (e.g., a memory stick, a hard disk, or another portable or integral data carrier), may be used on which the program sections of the computer program readable and executable from a processor unit of the control device are stored. The processor unit may have one or more collaborating microprocessors or the like. The processor unit may be part of a terminal or the control device of the magnetic resonance imaging system.

In an embodiment of the method, the corrected image data is generated on the basis of an iterative reconstruction in which the deformation fields are used to generate corrected raw data. Based on the deformation fields, additional raw data not available hitherto is generated and/or raw data already available assigned to other values of the movement parameters. The additionally generated raw data which is available for one or more sets of values of movement parameters of raw data may be used to assign raw data which has been incorrectly assigned to movement states to the correct movement states. In this manner, the image quality may be improved and/or movement artifacts may be reduced. Deformation fields are also determined by optimization. A known deformation field may be set as the starting point. The number of iterations in the optimization of the deformation fields may be established in a simple manner. The "determination" of deformation fields should also include the optimization of the deformation fields. Deformation fields and image data may also be optimized simultaneously and/or in a common optimization process.

In an embodiment of the method, the acquisition of raw data includes a Cartesian, potentially incomplete scan. In this context, an incomplete scan should be understood as a sub-sampling. Such a scan may be employed particularly advantageously for liver imaging as for such imaging the image displays are aligned in a head-foot direction and/or in an anterior-posterior direction.

In a variant of the method, the determination of deformation fields includes a registration of image data with at least partially different values of the time-dependent movement parameters. Shifts in the examination region are determined with the aid of the registrations. In this manner, image information assigned to certain values of movement parameters may also be assigned to other values so that the image quality for individual value tuples of movement parameters is improved.

In an embodiment of the method, the at least two different time-dependent movement parameters include at least two of the following types of parameter: the time, the movement state of respiration, the movement state of the heart.

Advantageously, a plurality of movement parameters is taken into account in the method. For example, with the aid of the deformation fields, raw data or image data assigned to the same movement state but assigned to a different time, may be combined and the image quality thus improved.

In a variant of the method, synthesized raw data is determined for the generation of corrected image data based on deformation fields for different values of the at least two time-dependent movement parameters. With the aid of the deformation fields, image data may be assigned to corrected positions. Based on the corrected assignment, synthesized raw data may then be generated with the help of which corrected image data may be reconstructed in turn.

In an embodiment of the method, based on the synthesized raw data, the acquired raw data is reassigned to changed values of movement parameters. For example, based on a comparison of the synthesized raw data with the acquired raw data, a false assignment of the acquired raw data may be detected and the acquired raw data may then be assigned to the correct movement states. In this manner, effects based on deformation which result in erroneous assignments of the raw data to individual movement states may be compensated. Erroneous assignments may also come about as a result of inaccurate measurement of movement states, for example, one-dimensional navigation. These errors may also be corrected by subsequent correction when assigning raw data to individual movement states.

Assignment to changed values of movement parameters may take place as a function of whether the conditions assigned to the values are similarly spaced from each other. In other words, the raw data determined for each measurement point is compared by a standard, distance measurement or correlation to the different synthetic measurement points/raw data and raw data is assigned to the movement state which is closer and/or has a greater correlation. The synthesized raw data points which are closest to the measured raw data points are therefore determined in a distance measurement or by correlation.

In a variant of the method, the reassignment of the raw data first takes place on the basis of a subset of the acquired raw data, (e.g., in a completely scanned direction, such as in a readout direction), and then the corrected image data is reconstructed on the basis of all the raw data.

In the second reconstruction, the assignment determined on the basis of the subset then takes place between raw data and movement states. No further state assignments are then changed in the process. Advantageously, time and data capacity may be saved with the aid of this approach. For example, a first reconstruction of image data may only take place initially on the basis of raw data acquired in a readout direction. This raw data is then used to determine deformation fields which are used in turn to correct the assignment of the acquired raw data.

In an embodiment of the method, items of raw data which differ in at least one of the at least two time-dependent movement parameters are discarded, and the corrected image data is only generated as a function of a subset of the at least two time-dependent movement parameters. Advantageously, the reconstruction time may be reduced on account of the reduced data processing.

In a completely scanned direction, orthogonal disks and/or disk-shaped layers may be reconstructed independently of one another. In order to reduce the computational complexity, the number of disks and/or layers may therefore be reduced so that the reconstructed image volume is reduced.

BRIEF DESCRIPTION OF THE DRAWINGS

The disclosure is explained again in more detail hereinafter with reference to the attached figures with the aid of exemplary embodiments, in which.

DETAILED DESCRIPTION

Figure 1:
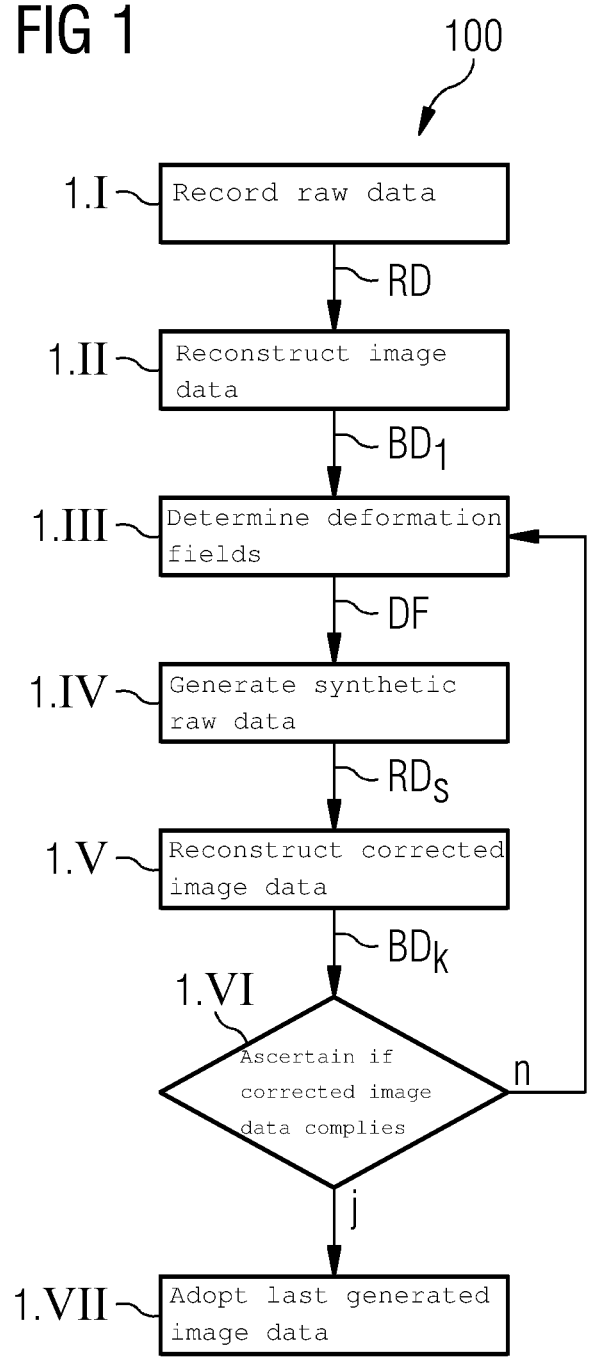
FIG. 1 depicts a flow chart which illustrates a method for reconstructing dynamic image data according to an exemplary embodiment.

FIG. 1 depicts a flow chart 100 which illustrates the method for reconstructing dynamic image data according to an exemplary embodiment.

In act 1.I, raw data RD from an examination region is first recorded. The examination region behaves dynamically during the acquisition of raw data RD, e.g., at least some of the raw data RD is assigned to different values of movement parameters $BP_r$. In act 1.II, first time-dependent image data BD1 is reconstructed on the basis of recorded raw data RD.

In act 1.III, deformation fields DF are determined on the basis of first image data BD1. The deformation fields DF depend on at least two time-dependent movement parameters, for example, the time t and the respiratory movement state AZ.

In act 1.IV, synthetic raw data $RD_s$ is generated with the aid of the first image data and the deformation fields DF.

Furthermore, in act 1.V, corrected image data $BD_k$ is reconstructed on the basis of synthetic raw data $RD_s$. In act 1.VI, it is ascertained whether the corrected image data $BD_k$ complies with a quality criterion crit. For example, the corrected image data $BD_k$ is inspected for artifacts. If the quality criterion has not yet been met, (which is characterized by "n" in FIG. 1), act 1.III is returned to, in which deformation fields DF, now however based on corrected image data $BD_k$, are generated again. Then the method is continued with acts 1.IV to 1.VI. In the event that act 1.VI ascertained that the quality criterion crit was met for the corrected images $BD_k$, (characterized by "y" in FIG. 1), then act 1.VII is commenced, in which the last generated image data $BD_k$ is adopted as final image data BD.

Figure 2:
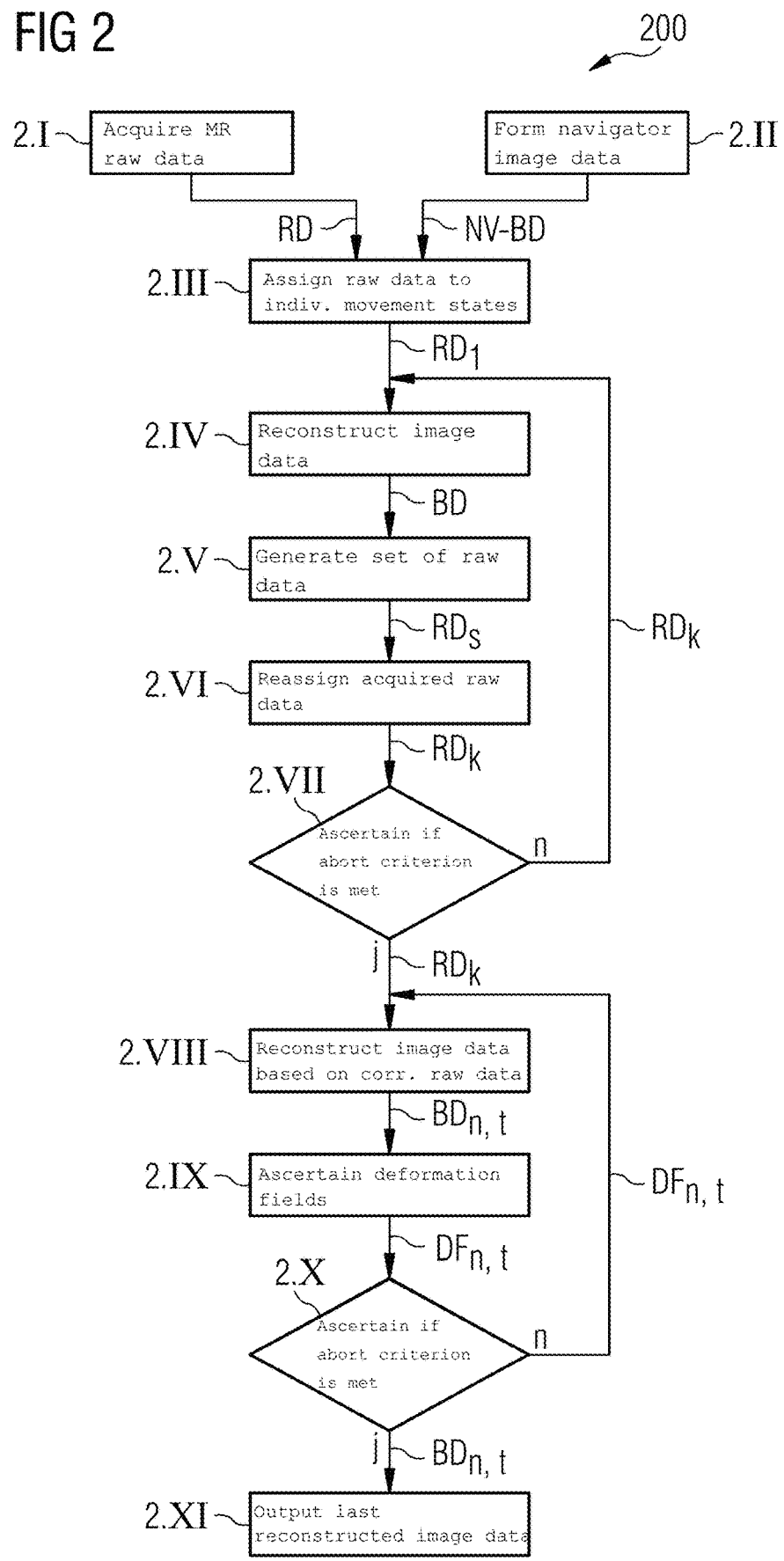
FIG. 2 depicts a flow chart which illustrates a method for reconstructing dynamic image data according to a second exemplary embodiment.

FIG. 2 depicts a flow chart 200 which illustrates the method for reconstructing dynamic image data according to a second exemplary embodiment.

In act 2.I, magnetic resonance raw data RD is first acquired from an examination region FoV of a patient. In addition, in act 2.II, Navigator raw data NV-RD is acquired and reconstructed to form Navigator image data NV-BD. The Navigator image data NV-BD characterizes a movement state of the examination region FoV for imaging. Based on the now known movement states and the raw data RD, in act 2.III raw data RD is now assigned to individual movement states, raw data $RD_1$ assigned according to movement state is therefore generated.

In act 2.IV, image data BD is reconstructed on the basis of raw data $RD_1$ assigned according to movement states. In the process, items of raw data, which are assigned to different times but the same movement states, are combined with one another. Furthermore, in act 2.V, a complete set of raw data with additional synthesized $RD_s$ is generated in the k-space for each movement state n and each time t, which replaces the raw data missing due to sub-sampling in raw data acquisition. In act 2.VI, the acquired raw data RD is then reassigned to the individual movement states by comparing the assignment of the acquired raw data RD and/or the classified raw data $RD_1$ to the assignment of the synthesized raw data $RD_s$. If applicable, corrected and/or reclassified raw data $RD_k$ is generated. Act 2.VII checks whether an abort criterion crit is met. In the event that the abort criterion has not yet been met, which is characterized by "n" in FIG. 2, act 2.IV is returned to and image data BD is reconstructed again based on the raw data $RD_k$ corrected in act 2.VI. Subsequently, acts 2.V and 2.VI are performed again. If an abort criterion crit is met in act 2.VII, for example, if a counting index has reached a maximum number of iterations for performance, which is characterized by "y" in FIG. 2, then act 2.VIII is commenced.

In act 2.VIII, image data $BD_{n,t}$ is reconstructed on the basis of corrected raw data $RD_k$ ascertained in act 2.VI which is classified according to movement state n and time t, wherein the images of different movement states are generated using deformation fields DF. In other words, the deformation fields DF are used to register image data of different movement states on top of one another in order to also obtain an adequate database for each of the movement states in a sub-sampling of individual movement states. For example, a matrix representing the identity may be used as an initial deformation field $DF_0$. Subsequently, in act 2.IX deformation fields $DF_{n,t}$ between different movement states and different times are ascertained on the basis of reconstructed image data $BD_{n,t}$. If an abort criterion crit is not met, (which is characterized by "n" in FIG. 2), in act 2.X, there is a return to act 2.VIII and image data $BD_{n,t}$ classified according to movement state and time is reconstructed in turn, but this time using the newly generated deformation fields $DF_{n,t}$ between different movement states n and different times t. If an abort criterion crit is met for iteration in act 2.X, (which is characterized by "y" in FIG. 2), then act 2.XI is commenced, in which the last reconstructed image data $BD_{n,t}$ is output as final image data BD.

Figure 3:
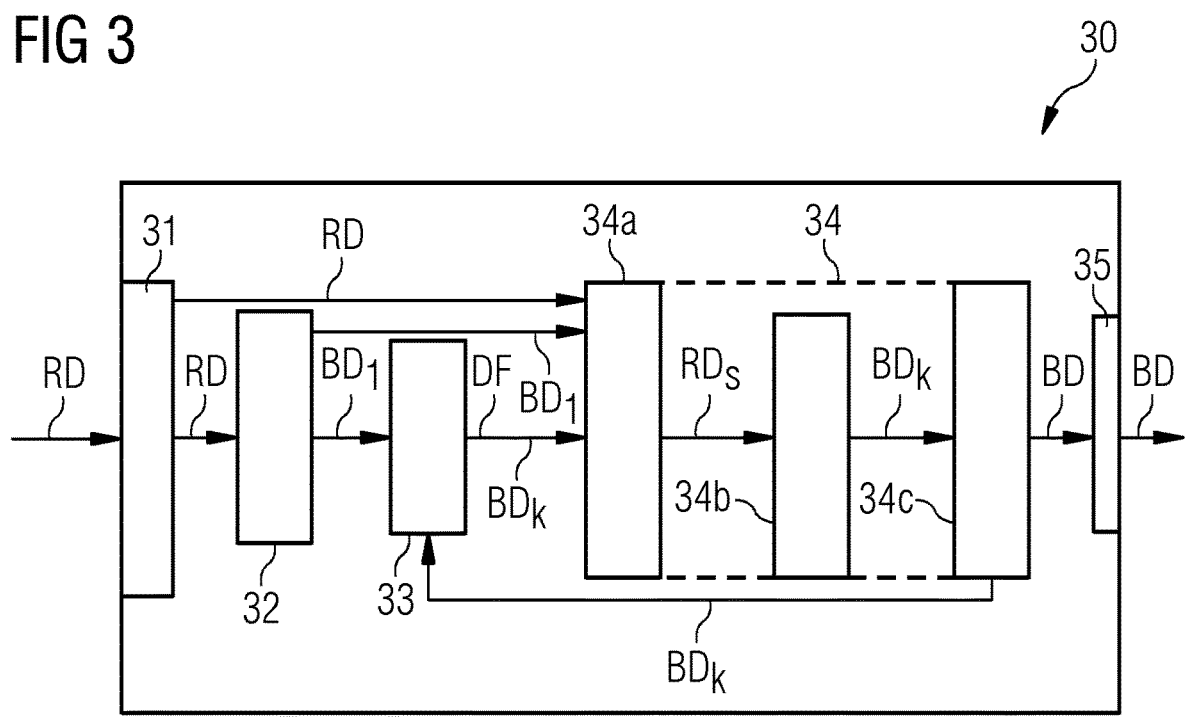
FIG. 3 depicts a block diagram which illustrates an image reconstruction apparatus according to an exemplary embodiment.

FIG. 3 illustrates an image reconstruction apparatus 30 according to an exemplary embodiment. The image reconstruction apparatus 30 includes an input interface 31 which is configured to receive raw data RD acquired in a time-dependent manner. At least some of the raw data RD is assigned to different values of movement parameters $BP_t$. The raw data RD is transmitted to a reconstruction unit 32, which reconstructs first time-dependent image data $BD_1$ on the basis of the acquired raw data RD. The image data $BD_1$ is forwarded to a deformation field determination unit 33, which determines deformation fields DF based on the first image data $BD_1$ as a function of at least two time-dependent movement parameters $BP_t$. The determined deformation fields DF and the received raw data RD and the reconstructed image data $BD_1$ are transmitted to a correction unit 34, which determines corrected image data $BD_k$ based on the deformation fields DF, the raw data and the first image data BD1.

The correction unit 34 includes a synthesization unit 34a, which generates synthesized raw data $RD_s$ based on the deformation fields DF, the raw data RD, and the image data BD1. Part of the correction unit 34 is also an image data reconstruction unit 34b, which reconstructs corrected image data $BD_k$ based on synthesized raw data $RD_s$. The corrected image data $BD_k$ is transmitted to a testing unit 34c, which is configured to test the corrected image data $BD_k$ with regard to the occurrence of artifacts. If the tested image data $BD_k$ does not yet meet a predetermined quality criterion, the corrected image data $BD_k$ is sent back to the deformation field determination unit 33, which generates corrected deformation fields DF based on corrected image data $BD_k$ which, together with the corrected image data $BD_k$, are in turn transmitted to the correction unit 34 from which corrected image data $BD_k$ is then generated again. If this complies with the aforementioned quality criterion, the last generated corrected image data $BD_k$ is established as the final image data BD and output by way of an output interface 35.

Figure 4:
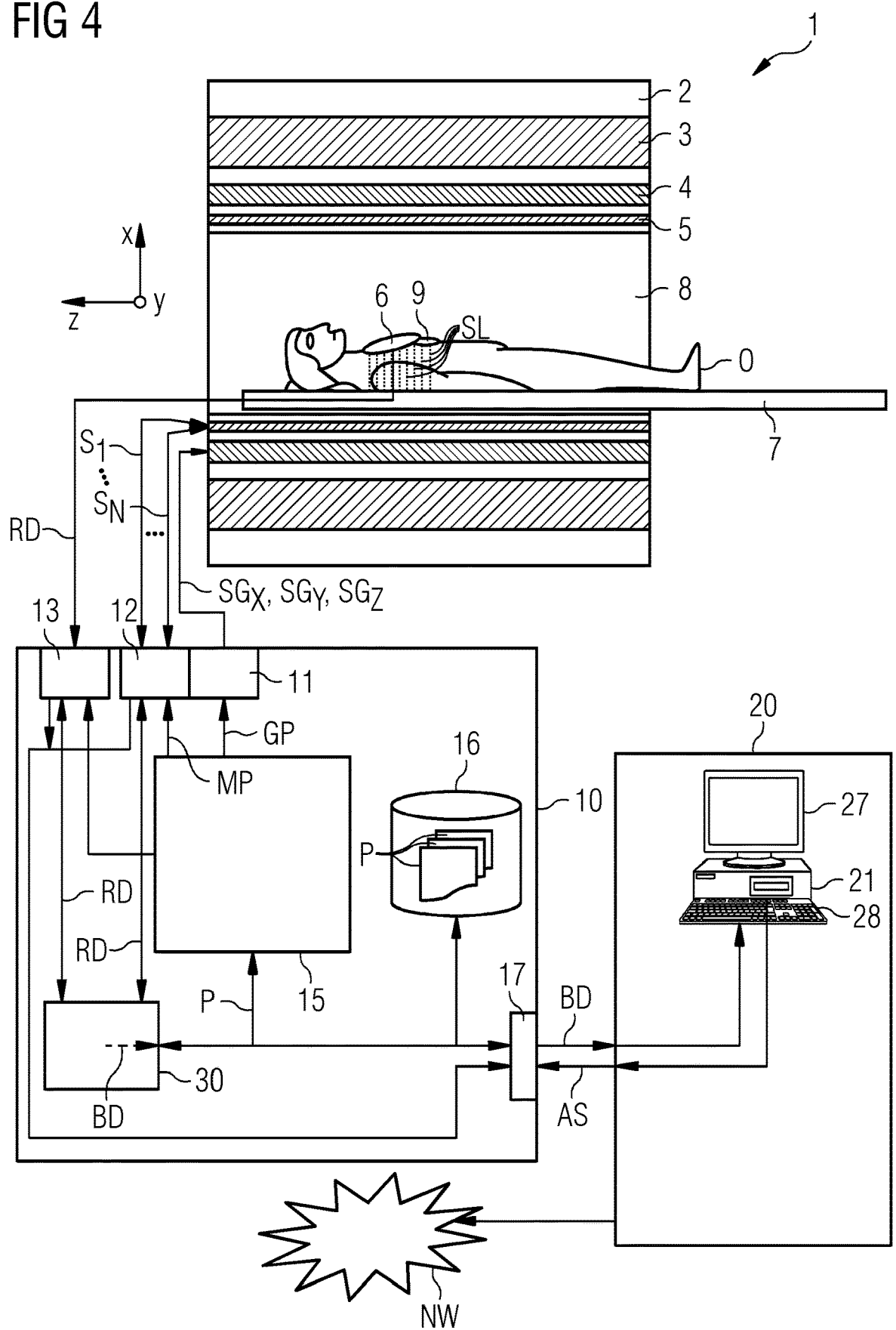
FIG. 4 depicts a diagrammatic view of a magnetic resonance imaging system according to an exemplary embodiment.

FIG. 4 diagrammatically outlines a magnetic resonance system and/or a magnetic resonance imaging system 1. This includes the actual magnetic resonance scanner 2 with a measuring area 8 and/or patient tunnel therein. A couch 7 may be moved into this patient tunnel 8 such that during an examination an examination object O (e.g., patient/subject) lying thereon may be accommodated in a particular position inside the magnetic resonance scanner 2 relative to the magnet system and high frequency system arranged therein and/or may also be moved between different positions during a measurement.

Components of the magnetic resonance scanner 2 include a basic field magnet 3, a gradient system 4 with gradient coils to create any magnetic field gradients in x, y, and z direction, and a whole-body radiofrequency coil 5. Magnetic resonance signals induced in the examination object O may be received by way of the whole-body coil 5 with which the radio frequency signals for inducing the magnetic resonance signals may also be emitted. These signals may be received with local coils 6 placed on or under the examination object O. In principle, all these components are known to a person skilled in the art and therefore only outlined diagrammatically in FIG. 4.

The whole-body radiofrequency coil 5 may have a number N of individual antenna rods which are separately controllable as individual transmit channels S1, . . . , SN from a control device 10, e.g., the magnetic resonance imaging system 1 is a pTX-capable system. However, it is expressly pointed out that the method is also applicable to traditional magnetic resonance imaging devices with only one transmit channel.

The control device 10 may be a control computer that includes a plurality of individual computers—if necessary, also spatially separated and connected to one another by way of suitable bus systems and/or cables or the like. This control device 10 is connected by way of a terminal interface 17 to a terminal 20, by way of which an operator may control the entire system 1. In the present case, this terminal 20 has a computer 21 with a keyboard 28, one or more monitors 27, and further input devices, (e.g., a mouse or the like), thus providing the operator with a graphic user interface.

The control device 10 has, inter alia, a gradient control unit 11 that may in turn include a plurality of subcomponents. The individual gradient coils are switched via this gradient control unit 11 with the control signals SGx, SGy, SGz. These are gradient pulses set at exactly scheduled time positions and with a predetermined temporal progression during a measurement to, for example, scan the examination object O and the assigned k-space in individual layers SL according to a control sequence AS.

Furthermore, the control device 10 has a radio-frequency transmitter/receiver unit 12. This RF transmitter/receiver unit 12 likewise includes a plurality of subcomponents to emit high frequency pulses in each case separately and parallel to the individual transmit channels $S_1$, . . . $S_N$, e.g., in this case to the individually controllable antenna rods of the body coil 5. Magnetic resonance signals may also be received via the transmitter/receiver unit 12. In this exemplary embodiment, however, this occurs with the aid of the local coils 6. The raw data RD received with these local coils 6 is read out and processed by an RF receiver unit 13. The magnetic resonance signals received from these or from the whole-body coil 5 by the RF transmitter/receiver unit 12 are transferred as raw data RD to an image reconstruction apparatus 30, which reconstructs the image data BD in the manner described in connection with FIG. 3 and stores it in a storage unit 16 and/or transfers it to the terminal 20 by way of the interface 17 so that the operator may view it. The image data BD may also be stored and/or displayed and evaluated at other sites via a network NW. Provided that the local coils 6 have a suitable switching unit, the local coils may also be connected to an RF transmitter/receiver unit 12 to also use the local coils for transmission, in particular in pTX mode.

The gradient controller 11, the RF transmitter/receiver unit 12, and the receiver unit 13 for the local coils 6 are activated, in each case coordinated by a measurement control unit 15. By corresponding commands, this provides that a desired gradient pulse train GP is emitted by appropriate gradient control signals SGx, SGy, SGz, and activates the RF transmitter/receiver unit 12 in parallel such that a multi-channel pulse train MP is emitted, e.g., that the appropriate radio-frequency pulses are provided in parallel on the individual transmit channels $S_1, \ldots S_N$ to the individual transmission rods of the whole-body coil 5. Furthermore, it is provided that the magnetic resonance signals to the local coils 6 are read out and processed by the RF receiver unit 13 and/or any signals to the whole-body coil 5 are read out and processed by the RF transmitter/receiver unit 12 at the appropriate time. The measurement control unit 15 specifies the corresponding signals, in particular, the multi-channel pulse train MP to the high frequency transmitter/receiver unit 12, and the gradient pulse train GP to the gradient control unit 11, according to a predetermined control protocol P. All the control data, which is adjusted during a measurement according to a predetermined control sequence AS, is stored in this control protocol P.

A plurality of control protocols P may be stored in a storage unit 16 for various measurements. These could be selected by the operator by way of the terminal 20, and if applicable, varied to then have an appropriate control protocol P available for the currently desired measurement with which the measurement control unit 15 may work. Otherwise, the operator may also call up control protocols P via a network NW, for example, from a manufacturer of the magnetic resonance system and then modify and use these, if need be.

The process of such a magnetic resonance measurement and the aforementioned components for activation are known to the person skilled in the art, however, and so they are not discussed in further detail here. Otherwise, such a magnetic resonance scanner 2 and the associated control device 10 may still have a plurality of further components which are likewise not described in detail here. It is noted at this point that the magnetic resonance scanner 2 may also be designed differently, for example, with a laterally open patient area, and that in principle the high frequency whole-body coil need not be designed as a birdcage antenna.

Finally, it is noted once again that in the case of the method and devices described above, they are exemplary embodiments of the disclosure and that the disclosure may be varied by the person skilled in the art without departing from the scope of the disclosure, insofar as it is specified by the claims. The method and the reconstruction apparatus were therefore primarily explained with the aid of a magnetic resonance system for recording medical image data. However, the disclosure is not limited to the application in the medical field but the disclosure may in principle also be applied to magnetic resonance systems for recording dynamic images for other purposes. For the sake of completeness, it is also noted that the use of the indefinite article "a" and/or "an" does not exclude the features concerned also being present several times. Likewise, the term "unit" does not exclude this including a plurality of components which may likewise also be spatially distributed.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for reconstructing dynamic magnetic resonance image data by a magnetic resonance imaging system, the method comprising:
   acquiring time-dependent magnetic resonance raw data from an examination region at a plurality of different times, wherein at least some of the acquired time-dependent magnetic resonance raw data is assigned to various values of at least two time-dependent movement parameters, and wherein the at least two time-dependent movement parameters comprise a time and a movement state of respiration or a movement state of a heart;
   reconstructing first time-dependent image data based on the acquired time-dependent magnetic resonance raw data;
   ascertaining deformation fields based on the first time-dependent image data as a function of the at least two time-dependent movement parameters;
   generating synthetic raw data for different values of the at least two time-dependent movement parameters based on the reconstructed first time-dependent image data and the ascertained deformation fields; and
   generating corrected image data based on the generated synthetic raw data.

2. The method of claim 1, wherein the generating of the corrected image data takes place based on an iterative reconstruction in which the deformation fields are used to generate corrected raw data.

3. The method of claim 2, wherein the acquiring of the time-dependent magnetic resonance raw data comprises a Cartesian scanning of magnetic resonance raw data.

4. The method of claim 3, wherein the ascertaining of the deformation fields comprises a registering of the first time-dependent image data with at least partially different values of the time-dependent movement parameters.

5. The method of claim 1, wherein the acquiring of the time-dependent magnetic resonance raw data comprises a Cartesian scanning of magnetic resonance raw data.

6. The method of claim 1, wherein the ascertaining of the deformation fields comprises a registering of the first time-dependent image data with at least partially different values of the time-dependent movement parameters.

7. The method of claim 1, further comprising:
   comparing the synthetic raw data and the acquired time-dependent magnetic resonance raw data;

detecting a false assignment of the acquired time-dependent magnetic resonance raw data to the at least two time-dependent movement parameters; and reassigning the time-dependent magnetic resonance raw data to changed values of the at least two time-dependent movement parameters based on the synthetic raw data.

8. The method of claim 7, wherein the reassigning to the changed values of the at least two time-dependent movement parameters takes place as a function of which synthetic raw data points of the synthetic raw data are closest to acquired magnetic resonance raw data points of the acquired time-dependent magnetic resonance raw data in a distance measurement or by correlation.

9. The method of claim 8, wherein the reassigning of the time-dependent magnetic resonance raw data is first performed on a subset of the acquired time-dependent magnetic resonance raw data and then the corrected image data is reconstructed based on all the acquired time-dependent magnetic resonance raw data.

10. The method of claim 9, wherein the subset of the acquired time-dependent magnetic resonance raw data is a subset in a fully sampled direction of the acquired time-dependent magnetic resonance raw data.

11. The method of claim 1, wherein acquired time-dependent magnetic resonance raw data categorized in at least one time-dependent movement parameter of the at least two time-dependent movement parameters are discarded and the corrected image data is only generated as a function of a subset of the at least two time-dependent movement parameters.

12. An image reconstruction apparatus of a magnetic resonance imaging system, the image reconstruction apparatus comprising:

an input interface configured to generate time-dependent magnetic resonance raw data from an examination region, wherein at least some of the time-dependent magnetic resonance raw data is associated with different values of at least two time-dependent movement parameters, and wherein the at least two time-dependent movement parameters comprise a time and a movement state of respiration or a movement state of a heart;

a reconstruction unit configured to reconstruct first time-dependent image data based on the time-dependent magnetic resonance raw data;

a deformation field determination unit configured to determine deformation fields based on first time-dependent image data as a function of the at least two time-dependent movement parameters; and a correction unit configured to: (1) generate synthetic raw data for different values of the at least two time-dependent movement parameters based on the reconstructed first time-dependent image data and the determined deformation fields, and (2) generate corrected image data based on the generated synthetic raw data.

13. A magnetic resonance imaging system comprising:

an image reconstruction apparatus comprising:

an input interface configured to generate time-dependent magnetic resonance raw data from an examination region, wherein at least some of the time-dependent magnetic resonance raw data is associated with different values of at least two time-dependent movement parameters, wherein the at least two time-dependent movement parameters comprise a time and a movement state of respiration or a movement state of a heart;

a reconstruction unit configured to reconstruct first time-dependent image data based on the time-dependent magnetic resonance raw data;

a deformation field determination unit configured to determine deformation fields based on first time-dependent image data as a function of the at least two time-dependent movement parameters; and a correction unit configured to: (1) generate synthetic raw data for different values of the at least two time-dependent movement parameters based on the reconstructed first time-dependent image data and the determined deformation fields, and (2) generate corrected image data based on the generated synthetic raw data.

14. The method of claim 1, further comprising:

assigning the acquired time-dependent magnetic resonance raw data to individual movement states, prior to the reconstructing of the first time-dependent image data.

15. The method of claim 2, wherein the iterative reconstruction comprises:

ascertaining whether the corrected image data complies with a quality criterion; and when the corrected image data does not comply with the quality criterion, iteratively repeating ascertaining new deformation fields based on the corrected image data, generating new synthetic raw data, and generating new corrected image data until the new corrected image data complies with the quality criterion.

* * * * *